(12) United States Patent
Fermi et al.

(10) Patent No.: US 12,096,949 B2
(45) Date of Patent: Sep. 24, 2024

(54) DEVICE FOR THE TREATMENT OF TISSUE CALCIFICATION

(71) Applicant: AorticLab Srl, Colleretto Giacosa (IT)

(72) Inventors: Enrico Fermi, Piacenza (IT); Enrico Pasquino, Savigny (CH); Stefano Osta, Saluggia (IT); Franco Osta, Pozzengo (IT); Francesco Bonetti, Turin (IT); Davide Benettin, Turin (IT)

(73) Assignee: AorticLab Srl, Colleretto Giacosa (IT)

( * ) Notice: Subject to any disclaimer, the term of this patent is extended or adjusted under 35 U.S.C. 154(b) by 546 days.

(21) Appl. No.: 17/418,874

(22) PCT Filed: Jan. 14, 2020

(86) PCT No.: PCT/EP2020/050778
§ 371 (c)(1),
(2) Date: Jun. 28, 2021

(87) PCT Pub. No.: WO2020/151995
PCT Pub. Date: Jul. 30, 2020

(65) Prior Publication Data
US 2022/0061869 A1 Mar. 3, 2022

(30) Foreign Application Priority Data
Jan. 24, 2019 (EP) .................... 19153513

(51) Int. Cl.
*A61B 17/22* (2006.01)
(52) U.S. Cl.
CPC ........ *A61B 17/2202* (2013.01); *A61B 2017/22008* (2013.01); *A61B 2017/22025* (2013.01);
(Continued)

(58) Field of Classification Search
CPC ...... A61B 17/2202; A61B 2017/22008; A61B 2017/22025; A61B 2017/22028;
(Continued)

(56) References Cited

U.S. PATENT DOCUMENTS

| 5,295,958 A | 3/1994 | Shturman |
| 8,083,707 B2 | 12/2011 | Tosaya et al. |

(Continued)

FOREIGN PATENT DOCUMENTS

| JP | 2008-522755 A | 7/2008 |
| JP | 2011-515188 A | 5/2011 |

(Continued)

OTHER PUBLICATIONS

Apfel, R. E., & Holland, C. K. (1991). Gauging the likelihood of cavitation from short-pulse, low-duty cycle diagnostic ultrasound. Ultrasound in medicine & biology, 17(2), 179-185.

(Continued)

*Primary Examiner* — Mohamed G Gabr
*Assistant Examiner* — Aman Kumar Mann
(74) *Attorney, Agent, or Firm* — Nixon & Vanderhye P.C.

(57) ABSTRACT

Device for the treatment of tissue calcification, in particular aortic valve leaflets, characterized by the fact that it comprises a first ultrasound emission source that is adapted to provide ultrasound waves with MHz frequencies and a second ultrasound emission source that is adapted to provide ultrasound waves with KHZ frequencies, both MHz and KHz waves being used for the said treatment. The invention also includes a method for the treatment of tissue calcification that is characterized by the simultaneous use of ultrasound waves with MHz frequencies and ultrasound waves with KHz frequencies.

15 Claims, 7 Drawing Sheets

(52) U.S. Cl.
CPC ............... *A61B 2017/22028* (2013.01); *A61B 2017/22079* (2013.01); *A61B 2017/22098* (2013.01)

(58) Field of Classification Search
CPC .......... A61B 2017/22007; A61B 17/22; A61B 2017/22098; A61N 2007/0039; A61N 2007/0073
See application file for complete search history.

(56) References Cited

U.S. PATENT DOCUMENTS

| | | | |
|---|---|---|---|
| 8,109,876 B1* | 2/2012 | Rambod | A61B 8/0833 600/437 |
| 10,238,895 B2 | 3/2019 | Sarge et al. | |
| 2010/0094209 A1 | 4/2010 | Drasler et al. | |
| 2011/0054363 A1* | 3/2011 | Cain | A61B 8/00 601/4 |
| 2011/0257562 A1 | 10/2011 | Schaer | |
| 2012/0109021 A1 | 5/2012 | Hastings et al. | |
| 2014/0163592 A1* | 6/2014 | Hawkins | A61B 17/22012 606/159 |
| 2015/0258352 A1* | 9/2015 | Lin | A61B 17/22004 601/2 |
| 2016/0135828 A1 | 5/2016 | Hawkins et al. | |
| 2016/0338724 A1* | 11/2016 | Sinelnikov | A61M 25/09 |
| 2020/0197033 A1 | 6/2020 | Pasquino et al. | |

FOREIGN PATENT DOCUMENTS

| | | |
|---|---|---|
| WO | WO 9217118 | 10/1992 |
| WO | 2005/094701 A1 | 10/2005 |
| WO | WO 2014022716 | 2/2014 |
| WO | 2014/114796 A1 | 7/2014 |
| WO | WO 2016077627 | 5/2016 |
| WO | 2018/211344 A1 | 11/2018 |
| WO | WO 2019053538 | 3/2019 |

OTHER PUBLICATIONS

Carabello, B. A., & Paulus, W. J. (2009). Aortic stenosis. The lancet, 373(9667), 956-966.
Feng, R., Zhao, Y., Zhu, C., & Mason, T. J. (2002). Enhancement of ultrasonic cavitation yield by multi-frequency sonication. Ultrasonics sonochemistry, 9(5), 231-236.
International Search Report mailed on May 25, 2020 for Application N° PCT/EP2020/050778.
Lernetti, G., Ciuti, P., Dezhkunov, N. V., Reali, M., Francescutto, A., & Johri, G. K. (1997). Enhancement of high-frequency acoustic cavitation effects by a low-frequency stimulation. Ultrasonics sonochemistry, 4(3), 263-268.
Liu, H. L., & Hsieh, C. M. (2009). Single-transducer dual-frequency ultrasound generation to enhance acoustic cavitation. Ultrasonics sonochemistry, 16(3), 431-438.
Written Opinion of the ISA mailed on May 25, 2020 for Application N° PCT/EP2020/050778.
Guo, S., Jing, Y., & Jiang, X. (2013). Temperature rise in tissue ablation using multi-frequency ultrasound. IEEE transactions on ultrasonics, ferroelectrics, and frequency control, 60(8), 1699-1707.
Hasanzadeh, H., Mokhtari-Dizaji, M., Bathaie, S. Z., Hassan, Z. M., Nilchiani, V., & Goudarzi, H. (2011). Enhancement and control of acoustic cavitation yield by low-level dual frequency sonication: a subharmonic analysis. Ultrasonics sonochemistry, 18(1), 394-400.
Pereira P. (2003). "Acoustics Beyond the Wave Equation".
Schmitz, C., Császár, N. B., Rompe, J. D., Chaves, H., & Furia, J. P. (2013). Treatment of chronic plantar fasciopathy with extracorporeal shock waves. Journal of orthopaedic surgery and research, 8(1), 1-11.
Zhou, Y. (2015). Principles and applications of therapeutic ultrasound in healthcare. CRC press. Chap 6.

* cited by examiner

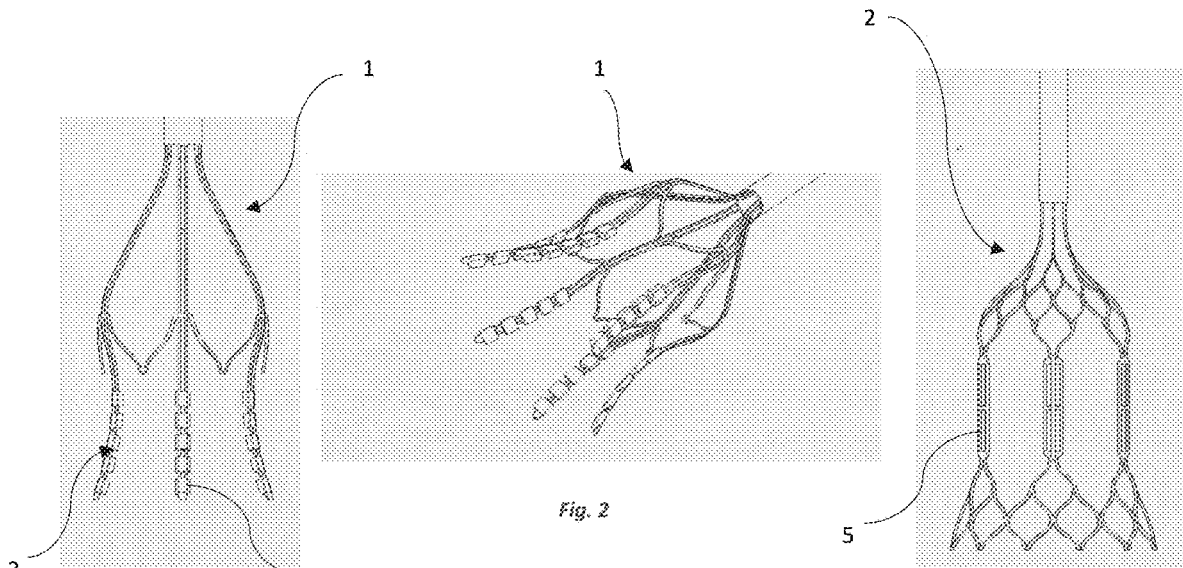
Fig. 1
Fig. 2
Fig. 3
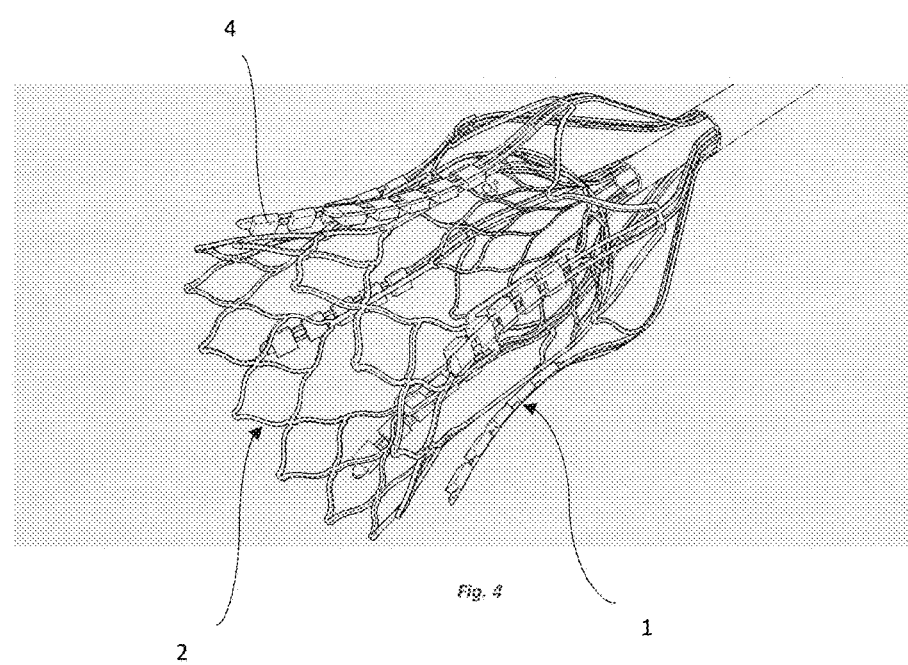
Fig. 4

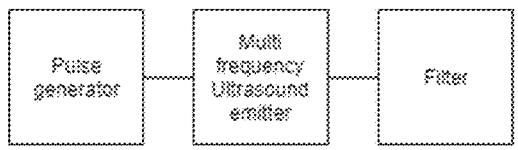
Fig. 5
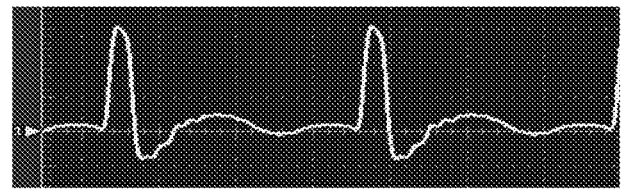
Fig 7
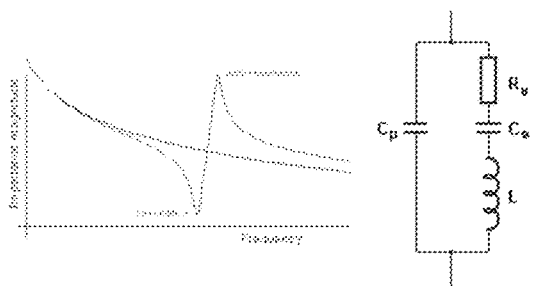
Fig.6
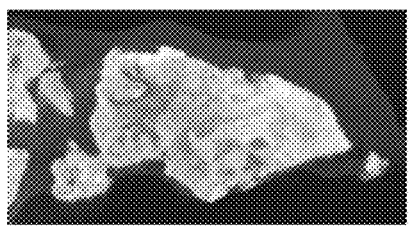
Fig. 8 Pre
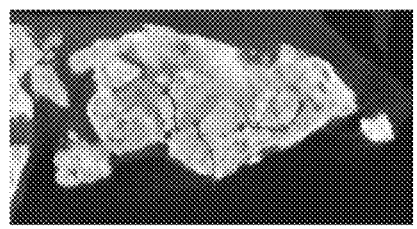
Fig. 8 Post Initial bubble radius (um)

DEVICE FOR THE TREATMENT OF TISSUE CALCIFICATION

CROSS REFERENCE TO RELATED APPLICATIONS

The present application is a United States national stage application of International patent application PCT/EP2020/050778 filed on Jan. 14, 2020, designating the United States, and claims foreign priority to European patent application No. EP 19153513.7 that was filed on Jan. 24, 2019, the contents of both these document herewith incorporated by reference in their entirety.

FIELD OF INVENTION

The present invention generally relates to the treatment of tissue calcification, in particular to the treatment of aortic leaflet calcification.

It more precisely relates to such a treatment by ultrasound waves.

STATE OF THE ART

Tissue calcifications, due to inflammatory conditions and specific biological processes, are common after 60 years of age.

Some disorders can cause calcium to deposit in ligaments, tendons, blood vessels, organs, particularly in the heart, in the mitral annulus or in the aortic leaflets, thereby altering their physiological functions.

Calcifications in the carotid arteries, in the anterior aorta, in the common or superficial femoral, in the tibial artery, in the heart valves, reduce the survival of the general population.

In particular, valvular aortic degenerative stenosis, typical of advanced age, has a prevalence of 3% in the Mediterranean area alone (4.6% for age >74 years) and reaches 10% in America and North America. According to Carabello, 2009, the prevalence of a clinically significant stenotic condition is about 20% in patients in the 65-75 age group, about 35% in the 75-85 age group and 48% in 85-percent patients.

The aortic valve is constantly subjected to repetitive mechanical stress, due to the contractions, to the consequent tissue deformation and to the transvalvular pressure gradient during the closing phase of each contraction (about 100 mmHg). Valvular calcification is the gradual accumulation of calcium and phosphate minerals: deposits that can thicken and form mineralized nodules. Deposits are concentrated in the areas most subjected to mechanical stress. It follows an impairment of cardiac hemodynamic. The pathogenesis of cardiac valvular calcifications is the result of a chronic inflammatory process.

Three essential types of aortic stenosis are recognized, for over 95% of the cases currently observable, namely:

AORTIC STENOSIS FROM DYSTROPHIC CALCIFICATION (65-70 YO): it is characterized by the absence of commissural fusion, preserving three independent leaflets. The stenosis derives from the stiffening of the leaflets, whose opening movement is strongly limited due to the presence of granules.

AORTIC STENOSIS FROM DYSTROPHIC CALCIFICATION OF BICUSPIDE VALVE (50-60 YO): The turbulent flow induced by the anomalous architecture of the valve traumatizes the leaflets, which undergo sclerosis and calcification.

AORTIC STENOSIS FROM CHRONIC REUMATIC VALVULITIS: the tricuspid architecture of the valve is preserved, but the three cusps are fused along the commissures, so that the orifice is reduced to a small round or triangular central opening.

The area of the aortic valve orifice should be reduced to less than ¼ of its normal size before significant hemodynamic changes occur. Starting from the onset of symptoms, the average survival can be as low as 2-3 years.

To prevent irreversible damage to the heart muscle, calcified aortic stenosis is, when possible, treated by surgery or trans-catheter TAVI, replacing the damaged valve with a valve prosthesis.

However, in some cases, surgery may be particularly risky, due to the patient's particular condition (for example, advanced age and other co-morbidities).

The transcatheter procedure, TAVI, is less invasive and can be applied to those patients that can't undergo the chirurgical procedure. However, in the case of very old age and comorbidity also TAVI is not recommended and these patients remain the only medical therapy with a low probability of survival at 2 years. In case of risk of procedural complications, risks of occlusion of the coronary hosts, or even for economic reasons, more than 200,000 patients, every year, are not treated.

Delaying replacement operations, restoring part of the valve function, or preparing the site to improve the effectiveness of TAVI are objectives that led to the realization of the following invention.

Patients who are not candidates for surgery or TAVI for valve replacement can benefit from a "decalcification procedure" in order to restore, partially, the valve functionality.

Ultrasonic waves, in particular shock waves, are daily used to treat calcifications in urological or orthopaedic fields and, to a less extend, in the vascular or cardiological field. An example of such a treatment in an implanted structure, such as a heart valve, is disclosed in U.S. Pat. No. 8,083,707 B2.

SUMMARY OF THE INVENTION

The present invention relates to a device and method that provide an improved tissue calcification treatment with respect to existing devices and methods.

The device according to the invention comprises a first ultrasound emission source that is adapted to provide ultrasound waves with MHz frequencies and a second ultrasound emission source that is adapted to provide ultrasound waves with KHz frequencies, both MHz and KHz waves being used for the treatment of tissue calcification.

The amplitude of one or all ultrasound emission sources can be varied, independently from each other, or in coordination.

The method according to the invention comprises the simultaneous use of ultrasound waves with MHz frequencies and ultrasound waves with KHz frequencies.

The MHz frequency is preferably selected between 3 and 4 MHz and the KHz frequency being preferably in the order of 100 KHz.

In the present invention, the expression "ultrasonic wave" has to be understood in its broadest definition. It includes any sound wave with a frequency above the upper audible limit of human hearing, usually in the order of 20 KHz. The ultrasonic wave used in the present invention may be generated in a continuous or discontinuous manner, e.g. by pulses.

In one preferred embodiment of the invention the two frequencies are in opposite directions with respect to the calcified zone.

More than two ultrasound emission sources can be used in the present invention, in any suitable geometry and/or configuration.

In one embodiment, to increase the area of the leaflet be treated with the device, without physically moving it, the ultrasound emission sources are configured in a phased array.

By varying the activation timing of each single emission source, (phase shifting), an interference is obtained between the single ultrasound fields generated, which leads to a focusing at a specific depth and specific angle. By varying the time delays appropriately, the focus area of the ultrasound field can be changed to the treatment, sweeping the beam on the leaflet.

The method of using ultrasonic fields and the mathematical justification of the choice of combining fields at least at two different frequencies is described in the next chapter.

When used for the treatment of an aortic valve, the device is preferably introduced by a catheter, designed for access via a femoral artery, into the seat of the aortic valve. The combined and simultaneous use of MHz and KHz frequencies induce an efficient fragmentation of the calcium deposits in the aortic valve leaflets. The device preferably comprises an antiembolic filter to capture any debris resulting from the decalcification treatment.

The device according to the invention provides several advantages, such as:
- restoring the flexibility of the treated tissue, for instance valve leaflets to recover a sufficient transvalvular flow/gradient;
- at least partially remove calcium from the native aortic valve, in order to obtain a more regular implant site and consequently optimize the implantation of a TAVI;
- partially eliminate calcium from valvular bio prostheses, to eliminate the structural deterioration caused by progressive calcification.

DETAILED DESCRIPTION OF THE INVENTION

The invention will be better understood below, in association with some illustrated examples.

Brief description of the Figures:

FIG. 1—First structure of a device according to the invention placed in the sinus of valve for the treatment of the aortic side of valve's leaflets and the combination with the low frequency field FIG. 2—view of the first structure of FIG. 1 with evidence of the 6 arms on which the piezoelectric transducers are mounted FIG. 3—Second structure positioned in the native aortic valve seat for the treatment of ventricular side of the valvular leaflets. The pillars keep the valve open. The piezoelectric transducers are mounted on the pillars for the creation of the low frequency ultrasonic "counter-field".

FIG. 4 Assembly view of first and second structures: the leaflets will be held back between the arms of the two structures.

FIG. 5 Block components diagram of the device

FIG. 6 Piezoelectric transducer equivalent circuit-Impedance diagram

FIG. 7 Pulse wave to power the piezoelectric transducers

FIG. 8 CT evidences of the treatment with ultrasound pulse waves: for reference see the fractures on the "Post" picture.

NUMERICAL REFERENCES USED IN THE FIGURES

Figure 9:
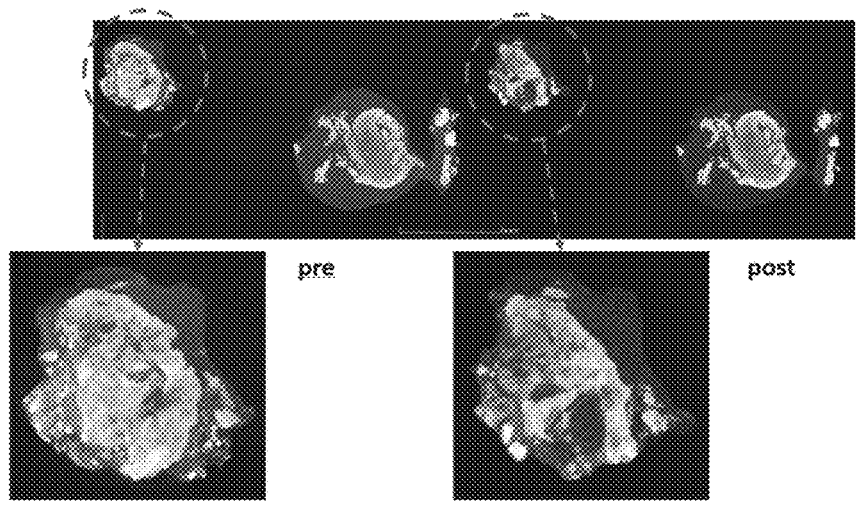
FIG. 9 CT evidence of calcific leaflet treated with pulse waves at a combination of two frequencies (Freq 1=3 MHz, Freq 2=100 KHz)
Figure 10:
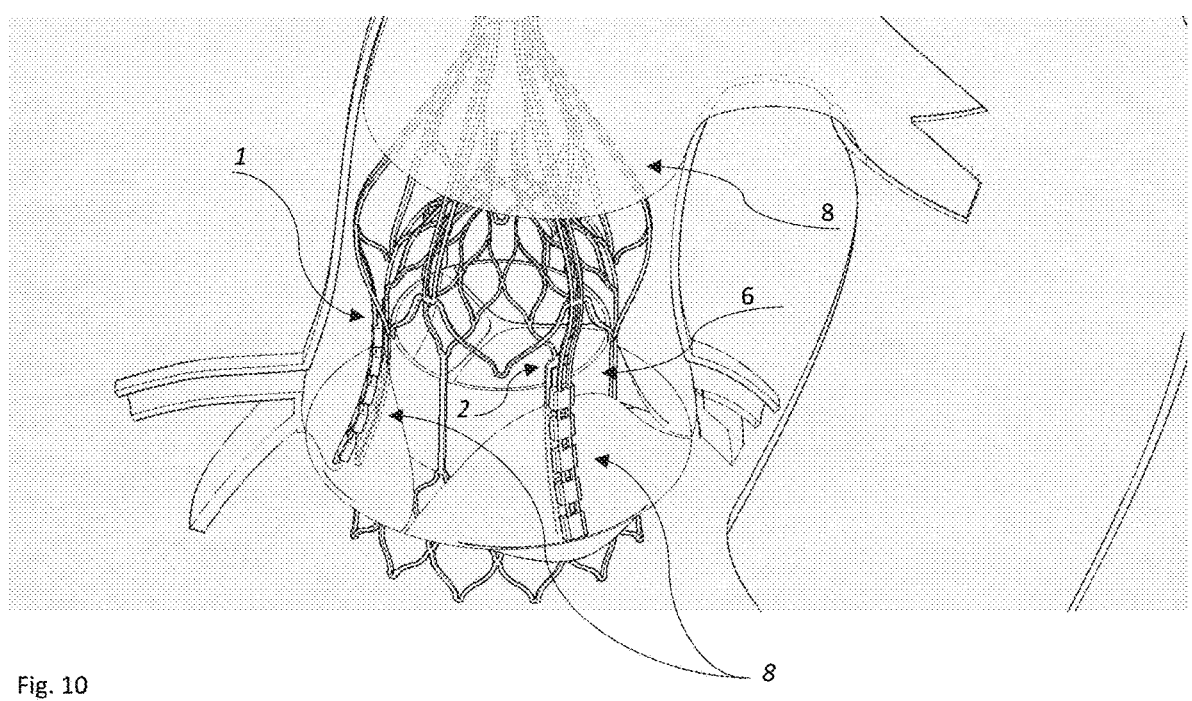
FIG. 10 First embodiment representation: the device is opened and positioned in the native valve with the valvular leaflets held back by the two "active" structures on which the piezoelectric transducers are "housed". In grey the artificial valve.

1. First structure
2. Second structure
3. Arm
4. Piezoelectric transducer first structure
5. Piezoelectric transducer second structure
6. Artificial valve
7. Native valve leaflet
8. Basket-Filter
9. Trapezium shaped support
10. First petal structure
11. Second petal structure
12. Upper base for housing the transducer operating preferably at 2-4 MHz
13. Lower base to preferably accommodate a 100 KHz transducer
14. Anchoring structure for steel or nitinol wires to move the "bunk structure"
15. "bunk structure" unit
16. Neodymium magnets (small squares)
17. Temporary valve
18. Single transducer
19. Deflector to protect coronary ostia In a first embodiment the device called "ablator" consists of three elements (FIG. 5):
1. a pulse wave generator at a peak voltage in the range of 20-100V
2. an ultrasound field emission unit, which can be positioned directly in the aortic valve seat, capable of providing temporary artificial valve function 3. a basket filter, made of porous fabric, for the collection of debris eventually released during the decalcification treatment.

The pulse generator can generate two impulsive signals simultaneously, in the range of 20-100V, with a positive peak followed by a negative peak, (FIG. 7), at 2 frequencies, one around 100 KHz and the second one in unit of MHz.

Unit 2 and 3 are conceived to be entirely collapsed inside a catheter and introduced in the patient's artery with the aim to reach the sinus of the valve and the valve itself and to be deployed in place.

The emission unit of the ultrasound field comprises two structures. The first structure 1 (FIG. 1) consists of multiple nitinol or steel arms 3 and is introduced through a femoral catheter, open and placed in the sinus of the valve. On the arms of the structure some piezoelectric transducers 4 are positioned, to generate the high frequency ultrasonic field, in the 2-4 Mhz range, for the treatment of the aortic side of the valve leaflets.

The piezoelectric transducers 4 are electrically connected in parallel to reduce the total impedance and increase the current circulating at the same supply voltage.

The shape of the arms 3 of this structure 1 has a bell section to adapt to the variability of the leaflets of the valve 8 opened, during treatment, from the second structure 2 (FIG. 3).

At least 6 arms 3 are necessary to treat simultaneously leaflets and commissures of the aortic valve. Three arms 3 with their piezoelectric transducers 4 are adapted to treat the leaflets creating the ultrasound counter-field opposite to the field generated by the second structure. The other arms 3 are devoted to treat the inter-leaflet triangle.

The second structure 2 integrates both the ablation function, with piezoelectric transducers 5 to generate the impulsive ultrasound waves, and the replacement valve function: positioned in the aortic valve seat, it keeps the leaflets 8 open with some pillars on which the piezoelectric crystals are positioned for treatment of the ventricular side of the valvular leaflets and for the creation of the low frequency ultrasonic "counter-field", in the order of thousands of Hz (e.g. 20 KHz or 100 KHz).

The combination of two fields with two frequency ranges, as described previously, improves the effectiveness of the decalcification treatment, keeping the energy used low so to avoid any dangerous temperature increases.

The second structure 2 provides an artificial valve 6 during the decalcifying treatment of the leaflets 8 of the native valve, kept open during operation.

The valve is made of leak-free coated fabric, for instance as disclosed in patent document PCT/IB2018/056553.

The device includes a "basket-shaped" filter 7 able to collect the debris produced by the disruption procedure of calcium deposits.

Through the delivery, introduced into the femoral artery, the valve seat is reached: the first 6-arm structure 1 is introduced into the sinus of the valve and opened. The second structure 2 follows and is placed in the native valve seat, opening the valve leaflets 8.

The valvular leaflets 8 are thus held back by the two structures 1,2. The ultrasonic field, emitted by electrically powered transducers 4,5 connected to the pulse generator, performs the decalcification treatment. The temperature is controlled by means of a thermocouple which supplies feedback to the pulse generator, which can interrupt the power supply of the transducers and consequently the therapeutic ultrasonic field.

During the treatment it is possible to monitor the systolic pressure gradient, with standard methods, and determine the EOA allowing the surgeon/interventional cardiologist to interrupt the treatment, depending on the level of restoration of the valve function reached.

Figure 11:
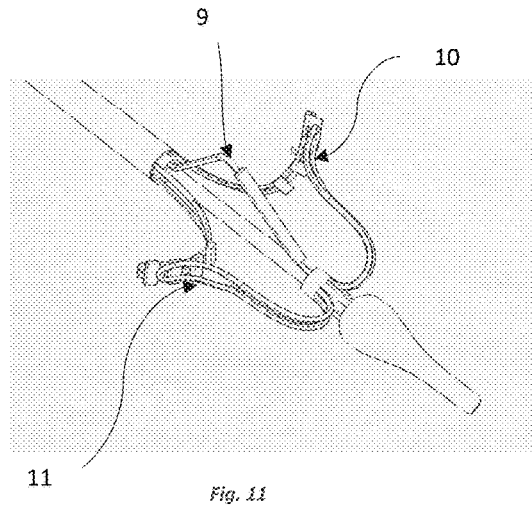
FIG. 11 The second embodiment with the ablator and its delivery system

In a second embodiment the ultrasound emission unit comprises three structures (FIG. 11):
- a trapezium shaped support 9 on which one or more piezoelectric plate transducers are housed, for the treatment and opening of the calcified commissure;
- a first structure 10 with 2 elements, similar in shape to "petals" on which several piezoelectric crystals are housed for the treatment from the out-flow side of the leaflet;
- a second 2-element structure 11 similar to the previous one, even if with different angles, with single piezoceramic transducer for each "petal", for the generation of the ultrasonic "counter-field".

This solution allows to treat a commissure and the two adjacent valve leaflets for each session, acting in particular on the nadirs of the semi-lunar leaflet attachment, without blocking the function of the cardiac valve.

Also, this embodiment can include a "basket-shaped" filter 7 able to collect the debris produced by the disruption procedure of calcium deposits.

Figure 12:
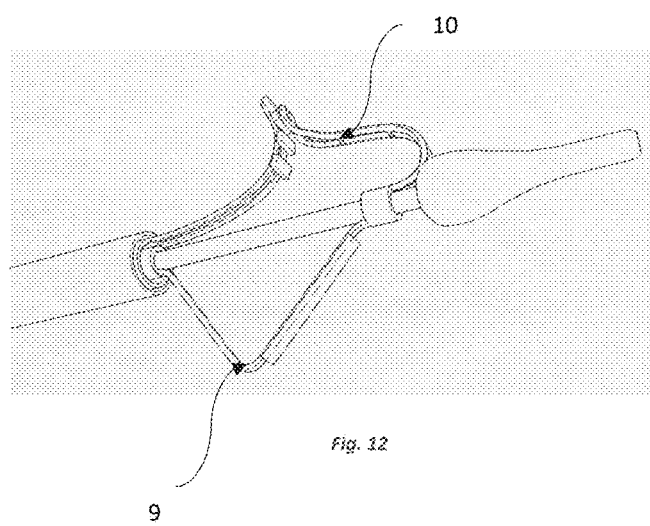
FIG. 12 Third embodiment ablator

In a third embodiment, derived from the second embodiment, there is only one "petal" structure 10 with several piezoelectric transducers housed, for the treatment of one aortic valve leaflet 8 and one arm of the support with one or more piezoelectric transducer, for the treatment of one commissure (FIG. 12).

In a fourth embodiment the ultrasonic field obtained by the combination of at least two frequencies, one in the order of 2-4 MHz and the second in the order of 100 KHz, is generated by two piezoelectric transducers positioned both on the extrados side of the aortic valve leaflet to be treated, placed side by side between them in parallel.

A combination of transducers and structural elements produces ultrasonic waves that interact with each other. The ultrasonic field is modulated by the combination of the two frequencies with "constructive" effects, ie the sum of the contributions.

Figure 14:
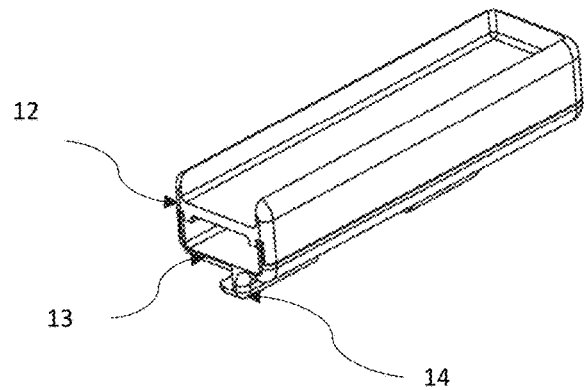
FIG. 14 Example according to the invention of a double support for the piezoelectric transducer called "bunk structure"

To support the transducers, a double layer structure called "bunk structure" is built. A possible realization has the shape represented in FIG. 14.

To ensure the necessary strength and mechanical rigidity, the "bunk structure" is preferably made of steel or titanium.

The transducer operating at a frequency of 100 KHz (+20 KHz) is housed in the lower base (13), while the second transducer operating at a frequency of 2-4 MHz is housed in the upper base (12).

In order to generate ultrasonic vibrations, a free space is left between the lower and upper transducers, at least twice the variation of the transducer length due to piezoelectric effect (usually the variation can be a small percentage, ie. between 0.1% and 0.15% of the size of the transducer. The distance is for instance 0.3 mm).

The electrical insulation of the transducers can be carried out by depositing a dielectric coating (e.g. Parylene) on the "bunk structure", with subsequent deposit of insulating coating on the whole assembled structure.

The electrical connection of the transducers takes place via enamelled copper wire soldered to the conductive armature of the transducers.

Other possibilities of electrical insulation can be obtained by interposing a flexible circuit of kapton (polyamide) between the piezoelectric transducer and the support base.

The flexible circuit can include small conductive areas to electrically connect the transducer.

On the lower base of the "bunk structure" there is an element for anchoring steel or nitinol wires in order to orient the structure.

Figure 15:
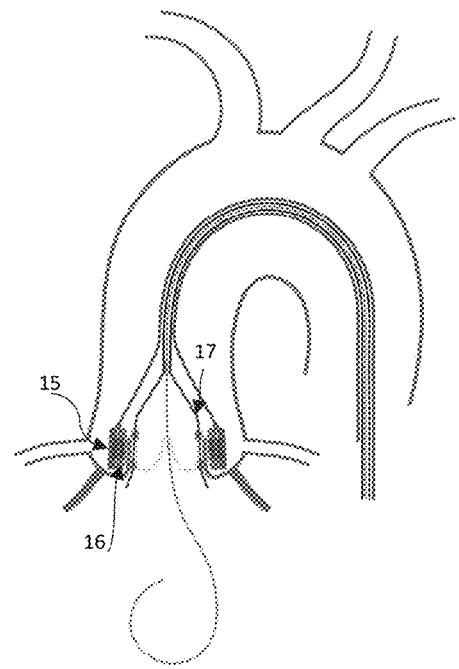
FIG. 15 Deployment with temporary artificial valve placed inside the patient's native aortic valve with two transducers placed on extrados side of the valve leaflets FIG. 16 Signal composed of pulse sequences at two different frequencies FIG. 17 Deployment with temporary artificial valve placed inside the patient's native aortic valve with a single transducer placed on extrados side of the valve leaflets FIG. 18 Example with deflector (in grey) anchored to the support structure FIG. 19 "Shockwave pulse" from ResearchGate, C. Schmitz et al.

This embodiment also includes an artificial temporary valve. The FIG. 15 shows the deployment with temporary artificial valve placed inside the patient's native aortic valve. The transducer supports (called ablation units) are positioned on the extrados side of the valve lealfets. Some neodymium magnets, or other materials with equivalent or superior magnetic properties, which help the positioning of the pair of transducers: the magnets included both on the valve structure and on the "bunk structures" attract each other, making the positioning "automatic". Magnets so help to place the pair of transducers in contact with the leaflet. In the FIG. 15 only one ablation unit is shown in the image, but the system can use 2 or 3 pairs of ablation units, for the simultaneous treatment of 2 or 3 leaflets. In this embodiment there are no transducers attached to the valve structure.

In a fifth embodiment the ultrasonic field is generated by a single piezoelectric transducer supplied with the two electrical signals at the two different frequencies, 100 KHz and 2-4 MHz, applied in sequence.

Figure 16:
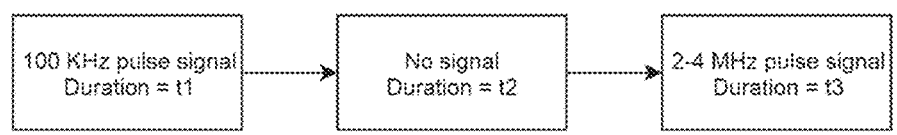

The supply signal is a pulse train with a positive peak followed by a negative peak, as described above, here modulated at the two different frequencies: the signal is a sequence composed of 100 KHz pulses for a duration $t_1$, followed by 2-4 MHz pulses for a $t_3$ duration, usually $t_3=2$ $t_1$ (i.e. t=5 s) (FIG. 16).

A short pause $t_2$, of a few milliseconds and however less than 1 second (i.e. 1 s or 500 ms or also a few milliseconds) between the two trains of impulses can be optionally considered to allow the transducer to reduce the oscillation before applying the different frequency.

To support mechanically the transducers, a structure made of steel or titanium is provided. The transducer is positioned in the notch of this support "frame".

Figure 17:
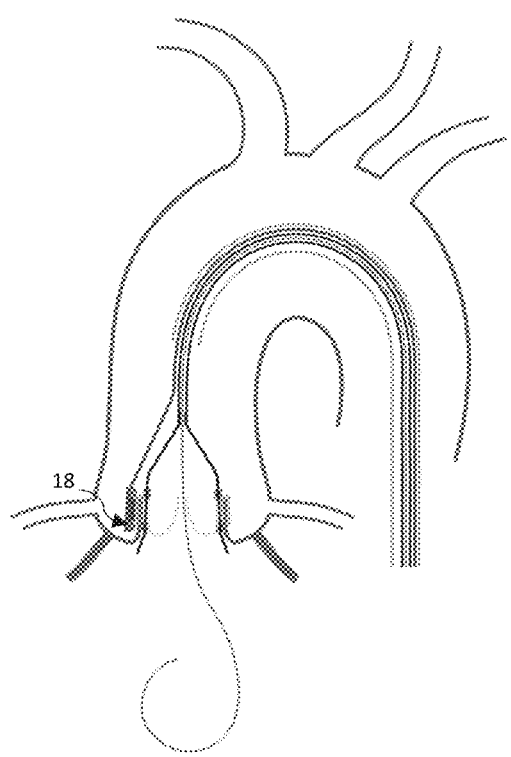

The device is assembled as in the previous embodiment, with the only difference given by the use of a single transducer with respect to the two transducers mounted on the "bunk structure" structure (FIG. 17).

It should be mentioned that with this fifth embodiment, the ultrasonic field can lead to the formation of a certain amount of bubbles with different rays, according to the frequency used.

The initial radius of the bubbles, in fact, is a function of the frequency used, for the same value of pressure, according to the equations of Minnaert ("The Minnaert bubble: an acoustic approach", European Journal of Physics 2008) and the approximation of Leighton ("The Acoustic Bubble", 1994).

Since the duration of these bubbles is greater than the time necessary to vary the frequency of the ultrasounds generated, it is possible to obtain the effect of cavitation that is the expansion and collapse of the bubbles, at different times. The lower frequency field nucleates larger bubbles while the higher frequency field, subsequently applied, creates the cavitation effect with the consequent growth and implosion of the bubbles obtaining a greater efficacy in the treatment of calcium deposits than the use of a single frequency.

Figure 18:
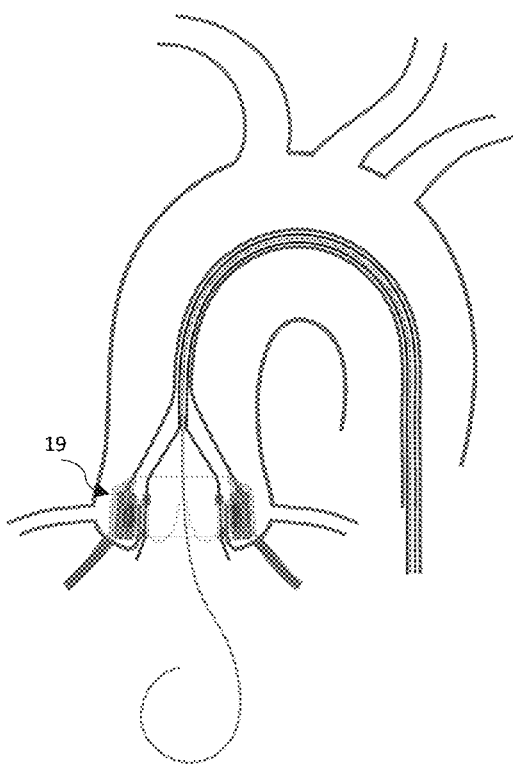

In a sixth embodiment is added a filter in polyester material or other equivalent material capable of deflecting in the blood stream, large amounts of debris and microaggregates from the blood. The filter is anchored to the outer side of the support structure of the piezoelectric transducers as shown in FIG. 18: the structure opens, stretching the polyester fabric or other equivalent material, providing protection to the coronary ostia.

Biophysical Analysis of the Combination of Ultrasonic Fields

Similar to lithotripsy, ultrasounds, properly modulated in intensity, frequency and waveform, can be used to produce fractures and structural changes in calcified deposits.

Energy levels that can be used in the field of vascular calcification have to be much lower than those used in the lithotripter. The pulse wave used in this method has a shockwave shape but a low energy, like the wave represented in the FIG. 6.

Ultrasonic shock waves can be generated in three different modes:

electro-hydraulic generator which consists of two electrodes which, through the emission of current, overheat the water in which they are immersed causing evaporation and consequently the increase in pressure that generates the shock wave.

electromagnetic generator, formed by a coil wire, wrapped by a metal membrane that generates a magnetic field at the passage of the current, which causes the membrane to expand, thus causing the formation of shock waves.

piezoelectric generator: the system uses piezoelectric crystals, or sonotrodes, immersed in water which, undergoing contractions and expansions of its volume, cause very little pressure waves in the water.

The object of the present invention uses the solution based on piezoelectric crystals to create low energy waves, which do not damage vital tissues. To achieve therapeutic efficacy, that is the disruption of calcium deposits, the method is based on the combination of different frequencies and the positioning of the transducers in opposite positions.

The acoustic pressure pulse or shock wave that "bump" on the calcification, acts directly on it as a force of mechanical stress and, indirectly, by the collapse of the cavitation bubbles formed inside the biological tissue.

The shockwave is a short-duration positive pulse, followed by a negative pressure pulse. The pressure curve describing the shock wave is characterized by an ascending phase in which the rise time, called "rise time" (Tr), can vary from a few nanoseconds (ns) to some microseconds (μs) and represents the time that the pressure takes up from 10% to 90% of its maximum value (Pmax). On the contrary, the wave trend in the descending phase of the curve is slower and irregular, before assuming negative value.

The ultrasonic field for therapeutic purposes to remove calcium deposits from the tissue, like heart valve leaflets, cannot involve the thermal increase that would damage the tissues, so the implementation of the invention exploits the combination of mechanical vibration and cavitation.

In the scientific literature the mechanism of action of the ultrasounds is described for disrupting calcific concretion. In particular impulse waves, in the form of a shockwave, which have, as described, at least two components, namely direct compression and negative tension, act on calcium deposits with combined effects of forces called "spallation" at the interface of tissue concretion, shear stresses and superfocusing.

It is therefore a combination of multiple effects of the incident acoustic wave to produce the breaking of the calcific deposits:

spallation occurs when the sonic wave crosses the calcification and is reflected on the back wall. The reflected impulse becomes a mechanical tension, which is more effective than the compression force (incident impulse);

shear forces resulting from a combination of compressive waves and transverse waves. The stratified and fragile conformation of calcium concretions has low resistance to transverse shear forces;

reflection of the "refracted" waves: the pressure waves passing through the concretion are reflected from several directions;

cavitation of the bubbles that form adjacent to the concretions, in the blood. The bubbles tend to form and "burst" (or to expand and then collapse), with the formation of microjets, mainly due to the effect of mechanical tension of the ultrasonic wave when it has negative amplitude;

fatigue: in the calcific deposits like in all solid structures subjected to mechanical stimuli, breakage can occur due to fatigue, usually where there are imperfections in which the effects of shock waves are concentrated.

superfocusing is created by the geometry of calcification as a combination of reflections and refractions of the waves that are focused within it.

A particular disruptive action on the deposited calcium, created by ultrasound, is given by the cavitation bubbles.

The phenomenon of cavitation can be seen as the "breaking" of a liquid and the consequent formation of bubbles, containing dissolved gas. The action of the ultrasonic field can create "acoustic" cavitation, distinct in "inertial" (transient) and "non-inertial" (stable). When a bubble is exposed to an ultrasonic field, the acoustic pressure acts as an external force that changes its radius. The bubble behaves like an oscillating system with an elasticity given by the gas contained inside it, and an inertia given by the liquid that surrounds the bubble and which oscillates with the wall of the bubble itself. The bubble therefore has its own frequency which is inversely proportional to its radius (in conditions of equilibrium).

The relationship between frequency of acoustic field and radius of the bubble can be simplified like this:

$$F \cdot R \approx 3$$

When the frequency of the acoustic field approaches the proper frequency of the bubble, resonant phenomenas occur: the bubble expands during the negative phase of the pressure wave and collapses very quickly and violently, at the arrival of the positive pressure. During the collapse the bubble can fragment and break or repeat the expansion and collapse cycles.

The explosion of the bubbles causes mechanical "erosion", due to the release of "concentrated" energy.

The frequencies normally used to induce cavitation, range from the order of tens of KHz to a few MHz. Higher frequencies induce thermal increase, controllable by reducing the amplitude of the wave. In the method described in this invention we consider low intensity so the thermal increase is negligible.

Cavitation requires initial conditions dependent on frequency (and temperature).

The minimum frequency of a shock wave source, which induces cavitation phenomena, is given by the definition of the mechanical index or MI (Mechanical Index):

$$MI = \frac{P_{neg}(MPa)}{\sqrt{f}}$$

Figure 19:
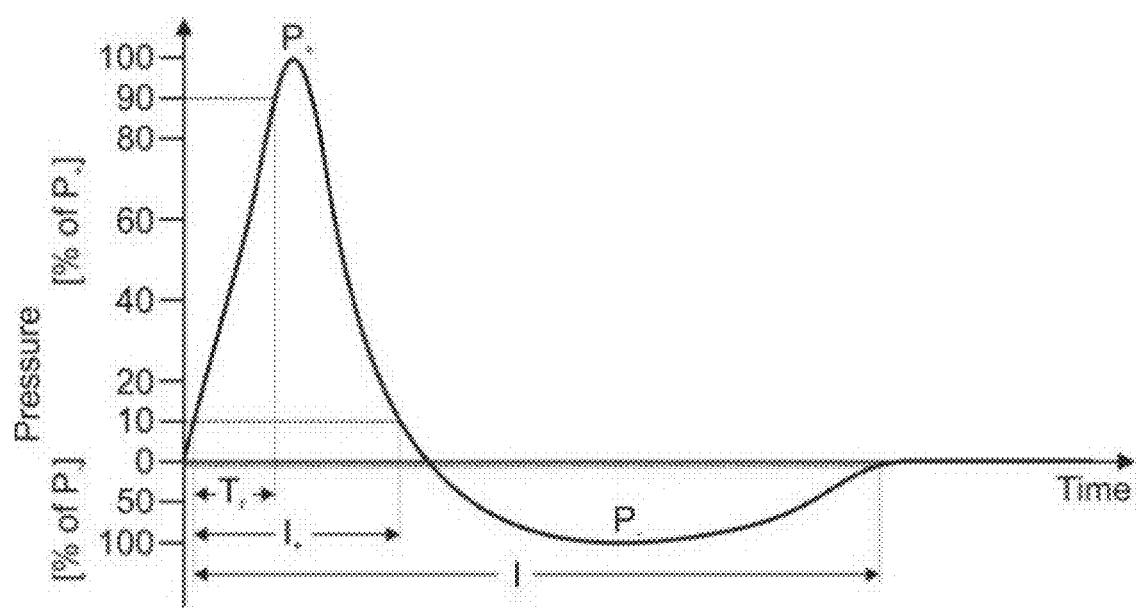

See FIG. 19—"Shockwave pulse" from ResearchGate, C. Schmitz et al.

At the peak of negative pressure, $P_{neg}$ corresponds to the maximum rarefaction of the acoustic wave.

There is cavitation when MI>0.7 MPa/MHz and so $P > 0.7 \cdot \sqrt{f}$

Figure 13:
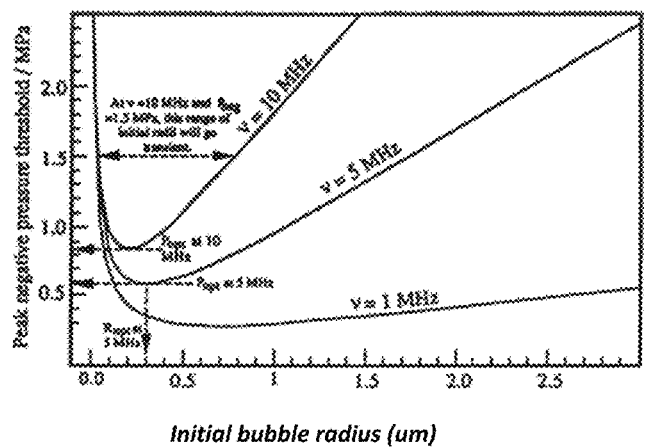
FIG. 13 Apfel, Holland, 1991 chart for 3 different frequencies. "Peak negative pressure threshold vs initial bubble radius".

For example, at a frequency of 10 Mhz, the minimum inertial pressure that causes cavitation is 0.84 MPa (and the bubbles with initial radius of 0.2 um begin to cavitate) (FIG. 13).

At frequencies of 3 and 4 MHz a negative peak of less than 0.5 MPa is sufficient to trigger cavitation.

Cavitation bubbles are inherently unstable, but repetition of impulses creates a "bubble cloud" confined to the focal volume of the ultrasound field.

The combination of frequencies has shown greater therapeutic efficacy, particularly in the fields of HIFU (high intensity focused ultrasound) use though the purpose is usually the thermal effect to "destroy" the tissue.

The hypothesis at the base of a higher efficacy is that the combination of multiple frequencies of the ultrasonic field directly affects cavitation.

There are some evidences in scientific literature to support this hypothesis.

E.g. Lernetti G. et al. In "Enhancement of high-frequency acoustic cavitation effect by a low-frequency stimulation", Ultrason. Sonochem, vol. 4, no. 3, pp. 263-268, 1997, demonstrates the increase in cavitation effect by combining two frequencies: 700 KHz and 20 KHz. In particular, low-frequency stimulation contributes by amplifying the effects of cavitation created by the higher frequency, also extending the cavitation volume.

Further enhancement is achieved by increasing the higher frequency. Feng et al. In "Enhancement of ultrasonic cavitation yield by multi-frequency sonication" Ultrason. Sonochem vol 9, no. 5, pp. 231-236, 2002 three frequencies are used (multibeam): 28 KHz, 1 MHz, 1.66 Mhz.

Bailey et al. combine a continuous wave at 250 kHz with a pulsed wave at 3 MHZ, achieving an intensification of the cavitation effects.

The same articles show how the combination of two sources at two different frequencies increases both the intensity and the bandwidth, "enhancing" the effect of the ultrasound field.

Furthermore, non-linear effects combined with the combination of the two frequencies reduce the threshold for generating cavitation effects. In ""Single-transducer dual-frequency ultrasound generation to enhance acoustic cavitation", Lu and al, 2008, show that the number of bubbles is 5 times higher by combining the 83 Khz and 271 KHz frequencies, compared to the 83 KHz frequency only, at a frequency of 83 KHz, at equal power supply, while a larger number of bubbles is obtained at lower power. The acoustic pressure and therefore the energy focuses, with the combination of frequencies, at a smaller distance of action.

In the combination of two field frequencies, the value of the higher frequency must be at least 500 KHz in turn "stimulated" or modulated by a frequency of the order of tens of KHz (Guo et al., 2013).

In "Enhancement of ultrasonic cavitation yield by multi-frequency sonication", Feng et al., Ultrasonics Sonochemistry 9 (2002) 231-236, at the cavitation enhancement contribute more elements:

the non-linear effects that lead to the formation of a larger number of bubbles with different rays;

the action of the forces of Bjerknes for the intensification of the fragmentation of the bubbles due to the interaction between the bubbles themselves;

formation of new cavitation nuclei due to the lower frequency, caused to implode by the higher frequency (the use of 3 frequencies in this case would further amplify the action)

The combination of frequencies makes the mass transfer between the liquid-gas phases more efficient.

The use of frequencies in the 2-4 MHz range allows to act on small diameter bubbles and to exert the action at a lower distance. The higher the frequency, the quicker the signal attenuates, "discharging" the energy at a short distance. The relation of acoustic attenuation with frequency is given by $\alpha=\alpha_0 f^2$ The distance is instead calculated as 1 dB/cm/MHz×f× (2×max depth)=65 dB The temperature also influences the cavitation threshold: in particular with increasing T, the vapor pressure decreases and cavitation occurs at a lower field strength.

For sufficiently large values of acoustic pressure together with a non-zero flow velocity of the fluids, the average value of the acoustic variables is not zero and linear acoustics is not applicable.

For a one-dimensional wave that propagates along X axis, the non-linear, dynamic and continuity equations are:

$$\frac{\partial v}{\partial t} + \frac{1}{2}\frac{\partial v^2}{\partial x} = -\frac{1}{\rho}\frac{\partial p}{\partial x}$$

$$\frac{\partial \rho}{\partial t} + \frac{\partial}{\partial x}(\rho v) = 0$$

and as a function of the potential flow:

$$\frac{\partial^2 \phi}{\partial t^2} - c_0^2 \frac{\partial^2 \phi}{\partial x^2} = \frac{\partial}{\partial t}\left[\left(\frac{\partial \phi}{\partial x}\right)^2 + a\left(\frac{\partial \phi}{\partial t}\right)^2\right]$$

where $\alpha=(\gamma-1)/2c_0^2$

We refer to the physical theory the solution of the equation (approximated by the "small-disturbance" theory, that provides the first and second harmonic (considering $\phi=\phi_1+\phi_2$, first and second order of the approximation) with pressures given by:

$$p_1 = \rho_0 \frac{\partial \phi_1}{\partial t} = p_{1a}\sin\omega\left(t - \frac{x}{c_0}\right)$$

$$p_2 = \rho_0 \frac{\partial \phi_2}{\partial t} = \frac{(\gamma+1)\omega x p_{1a}^2}{4\rho_0 c_0^3}\sin2\omega\left(t - \frac{x}{c_0}\right)$$

where $$p_{1a} = \rho_0 \phi_a \omega e p_{2a} = \frac{(\gamma+1)\omega x p_{1a}^2}{4\rho_0 c_0^3}$$

Consider here two different sources that interact, with different values of angular frequency, one greater than the other ($\omega_2 > \omega_1$)

$$p_1 = p_{1a}\sin\omega_1\left(t - \frac{x}{c_0}\right) + p_{2a}\sin\omega_2\left(t - \frac{x}{c_0}\right)$$

with $p_{1a}=\rho_0\omega_1\phi_{1a}$ e $p_{2a}=\rho_0\omega_0\phi_{2a}$ $$p_2 = \frac{(\gamma+1)\omega_1 x p_{1a}^2}{4\rho_0 c_0^3}\sin2\omega_1\left(t - \frac{x}{c_0}\right) +$$

$$\frac{(\gamma+1)\omega_2 x p_{2a}^2}{4\rho_0 c_0^3}\sin2\omega_2\left(t - \frac{x}{c_0}\right) + \frac{(\gamma+1)x p_{1a} p_{2a}}{4\rho_0 c_0^3}$$

$$\left\{(\omega_2 - \omega_1)\sin\left[(\omega_2 - \omega_1)\left(t - \frac{x}{c_0}\right)\right] + (\omega_2 - \omega_1)\sin\left[(\omega_2 - \omega_1)\left(t - \frac{x}{c_0}\right)\right]\right\}$$

$$p_2 = p_{2\omega_1} + p_{2\omega_2} + p_{(\omega_1 \pm \omega_2)}$$

The equation demonstrates the interaction and "amplification" of the effects of the waves.

To consider the propagation medium, consisting of calcified biological tissue and the presence of blood, we apply the eq. of Westervelt that allows to describe the propagation of the acoustic wave in these conditions, in particular in the presence of thermoviscous liquid (nonlinear propagation):

$$\nabla^2 p - \frac{1}{c_0^2}\frac{\partial^2 p}{\partial t^2} + \frac{\delta}{c_0^4}\frac{\partial^4 p}{\partial t^3} = -\frac{\beta}{\rho_0 c_0^2}\frac{\partial^2 p^2}{\partial t^2}$$

Where
p acoustic pressure
$c_0$ sound velocity
$\delta$ sound diffusion coefficient
$\beta$ non-linearity coefficient
$\rho_0$ density of the medium (environment)

$$\delta = \frac{1}{\rho_0}\left(\frac{4}{3}\mu + \mu_B\right) + \frac{k}{\rho_0}\left(\frac{1}{c_v} - \frac{1}{c_p}\right)$$

with
$\mu$ viscosity coefficient shear forces
$\mu_B$ volume viscosity coefficient
k thermal conductivity
Cv and Cp specific heat at volume and constant pressure The right side of the eq. of Westervelt, corresponding to the non-linear contribution, describes the effect of the spatial distribution of "virtual acoustic sources" created by sound waves *: Westervelt noted that non-linear interactions between two sources act as a spatial distribution of sources ("virtual" sources) **. The two different frequencies of the sources, due to the non linear behavior, produce effects given by their sum and their difference.

* "Principles and Application of Therapeutic Ultrasound in Healthcare", Cap. 6
** "Acoustics Beyond the Wave Equation", P. Pereira, 2003

The calculation of the acoustic pressure generated by the ultrasonic field combined from two sources at different frequencies can be made by the Rayleigh-Sommerfeld integral.

For two sources at the same continuous frequency, the integral provides the estimate of the acoustic pressure given by the sum of the contributions of a source to r' towards a point r, and becomes:

$$\hat{p}(x, y, z) = \frac{i\rho ck}{2\pi} \int_S \frac{ue^{-ik(r-r')}}{r-r'} ds$$

where ρ is the density of the tissue, c the speed of sound, k the wave number (2π/λ), u is the complex surface speed. For two excitation frequencies, the absolute value of p becomes $$p_{mixed}(x,y,z) = |\hat{p}_{f1(x,y,z)} + \hat{p}_{f2(x,y,z)}|$$

This demonstrates how the combination of at least 2 different frequencies allows to amplify the effect of the ultrasound field.

Dimensions of Piezoelectric Transducers

The dimensions of the piezoelectric transducers are chosen as a function of the field frequency to be generated which corresponds to their series resonance frequency (FIG. 1).

Electrical Connection of Piezoelectric Transducers in Parallel

The transducers can be connected in parallel to decrease the impedance value and increase the power of the emitted field accordingly, without changing the voltage and the power supply current.

Evidences of the Efficacy of the Combined Ultrasonic Fields

Numerous in-vitro tests have been performed, applying the method described in this invention on calcified valvular leaflets. The combination of two-frequency fields, one at 2-4 MHz and the second at about 100 KHz, produces effects of removal and reduction of calcium deposits higher than the use of a single ultrasound field. FIGS. 8 and 9 are CT scan of the calcified leaflets, pre and post treatment. FIG. 9 shows a treatment performed with a combination of ultrasonic fields at the two frequencies mentioned, while FIG. 8 shows the effects obtained with the use of a single ultrasound field. A greater reduction of calcium is shown in the CT scan of FIG. 9, compared to the simple fractures that can be observed in FIG. 8, demonstrating the greater effectiveness of the method.

The same invention can be used for the treatment of generic tissue calcifications like those in ligaments, tendons, blood vessels, (carotid arteries, in the anterior aorta, in the common or superficial femoral, in the tibial artery), organs.

The invention claimed is:

1. A device for the treatment of tissue calcification comprising:
   a first ultrasound emission source configured to provide ultrasound waves with frequencies between 2 MHz and 4 MHz; and
   a second ultrasound emission source configured to provide ultrasound waves with frequencies between 80 KHz and 120 KHz,
   wherein both ultrasound waves with MHz and KHz frequencies are configured to be used for the treatment;
   the device further comprising two structures including,
      a first structure configured to be positioned in a sinus of a Valsalva, the first structure having a plurality of piezoelectric transducers for treating an aortic side of the calcified aortic leaflet, and
      a second structure insertable to a native valve seat, the second structure configured to maintain a native valve open by a pillars on which a plurality of piezoelectric transducers are arranged.

2. The device according to claim 1, configured for the treatment of a calcification of an aortic leaflet.

3. The device according to claim 2, wherein the first and second ultrasound emission sources are configured to generate ultrasound waves in opposite directions to simultaneously treat an aortic side and a ventricular side of the aortic leaflet.

4. The device according to claim 1, further comprising:
   a basket-shaped filter configured to collect debris produced during the treatment.

5. The device according to claim 1, wherein the first and second ultrasound emission sources are located within a same element.

6. The device according to claim 5, wherein the same element includes a single piezoelectric transducer.

7. The device according to claim 1, wherein the first structure includes three (3) arms for the treatment the calcified aortic leaflet.

8. The device according to claim 1, wherein the first structure comprises six (6) arms for a simultaneous treatment of the calcified aortic leaflet and commissures.

9. The device according to claim 1, wherein the first structure includes a bell section configured to adapt to a variability of leaflets of the native valve.

10. The device according to claim 1, further comprising:
    an integrated artificial valve configured to work temporarily during the treatment.

11. The device according to claim 10, wherein the artificial valve is fixed to the second structure.

12. A system for treatment of a calcification of an aortic leaflet comprising:
    a device according to claim 1; and
    a coronary artery protection deflector that is integrated into the first structure.

13. A method for the treatment of tissue calcification, using the device of claim 1, comprising the steps of:
    first irradiating calcified tissue with an ultrasound wave having MHz frequencies;
    and second irradiating calcified tissue with an ultrasound wave having KHz frequencies,
    wherein the steps of first and second irradiating are performed simultaneously.

14. The method according to claim 13, wherein an emission direction of the first irradiating and the emission direction of the second irradiating are opposite to each other.

15. The method according to claim 13 for the treatment of a calcification of the aortic leaflet.

\* \* \* \* \*